(12) United States Patent
Schmidt et al.

(10) Patent No.: US 11,317,476 B2
(45) Date of Patent: Apr. 26, 2022

(54) EVAPORATOR UNIT FOR AN INHALER AND METHOD FOR CONTROLLING AN EVAPORATOR UNIT

(71) Applicant: HAUNI MASCHINENBAU GMBH, Hamburg (DE)

(72) Inventors: Rene Schmidt, Buchholz (DE); Marc Kessler, Hamburg (DE)

(73) Assignee: HAUNI MASCHINENBAU GMBH, Hamburg (DE)

( * ) Notice: Subject to any disclaimer, the term of this patent is extended or adjusted under 35 U.S.C. 154(b) by 494 days.

(21) Appl. No.: 15/988,730

(22) Filed: May 24, 2018

(65) Prior Publication Data

US 2018/0360116 A1  Dec. 20, 2018

(30) Foreign Application Priority Data

May 24, 2017 (DE) .................... 10 2017 111 435.1

(51) Int. Cl.
  *A24F 40/10* (2020.01)
  *H05B 3/34* (2006.01)
  (Continued)

(52) U.S. Cl.
  CPC ............. *H05B 3/34* (2013.01); *A24B 15/167* (2016.11); *A24F 40/44* (2020.01); *A24F 40/46* (2020.01);
  (Continued)

(58) Field of Classification Search
  CPC ... A61M 15/06; A61M 15/0001; A24F 40/00; A24F 40/10; A24F 40/40; A24F 40/51;
  (Continued)

(56) References Cited

U.S. PATENT DOCUMENTS 5,144,962 A    9/1992 Counts et al.
9,555,199 B2 * 1/2017 Buchberger ......... A61M 11/042
(Continued)

FOREIGN PATENT DOCUMENTS

DE         690 17 371       10/1995
DE    10 2016 120 803 A1     5/2018
(Continued)

OTHER PUBLICATIONS

European Search Report dated Oct. 12, 2018 issued by the European Patent Office with respect to the parallel European Patent Application No. 18 172 913.8-1204.
(Continued)

*Primary Examiner* — Michael J Felton
*Assistant Examiner* — Yana B Krinker
(74) *Attorney, Agent, or Firm* — Saliwanchik, Lloyd & Eisenschenk

(57) ABSTRACT

An evaporator unit for an inhaler comprising a heating element is designed to evaporate liquid, the evaporated liquid being taken up by an airflow flowing through the evaporator unit. The evaporator unit comprises at least one air-permeable capillary structure having a surface that is heatable in order to preheat the liquid and can be wetted, at least in part, by liquid and is supplied with liquid by capillary action, and the heating element is designed to heat the airflow flowing through the evaporator unit, the capillary structure being arranged downstream of the heating element such that the heated airflow leads to evaporation of the preheated liquid.

20 Claims, 4 Drawing Sheets

(51) Int. Cl.
*H05B 1/02* (2006.01)
*A24F 40/46* (2020.01)
*A24F 40/44* (2020.01)
*A24F 40/485* (2020.01)
*A24F 40/50* (2020.01)
*A24B 15/167* (2020.01)
*A61M 11/04* (2006.01)

(52) U.S. Cl.
CPC ............ *A24F 40/485* (2020.01); *A24F 40/50* (2020.01); *H05B 1/0227* (2013.01); *H05B 1/0297* (2013.01); *A24F 40/10* (2020.01); *A61M 11/042* (2014.02); *H05B 2203/021* (2013.01); *H05B 2203/022* (2013.01)

(58) Field of Classification Search
CPC .......... A24F 40/53; A24F 40/57; A24F 47/00; A24F 47/002; A24F 47/008
See application file for complete search history.

(56) References Cited

U.S. PATENT DOCUMENTS

| | | | | |
|---|---|---|---|---|
| 2015/0282526 A1* | 10/2015 | Wu | ............... | H05B 1/0244 |
| | | | | 131/329 |
| 2015/0351456 A1* | 12/2015 | Johnson | ............... | A24F 40/30 |
| | | | | 131/329 |
| 2015/0359263 A1* | 12/2015 | Bellinger | ............... | A24F 47/008 |
| | | | | 392/394 |
| 2016/0007653 A1* | 1/2016 | Tu | ............... | A24F 40/70 |
| | | | | 392/403 |
| 2016/0021930 A1* | 1/2016 | Minskoff | ............... | A61M 11/041 |
| | | | | 131/329 |
| 2016/0262454 A1* | 9/2016 | Sears | ............... | A61M 11/042 |
| 2016/0338410 A1* | 11/2016 | Batista | ............... | A24F 40/46 |
| 2016/0353802 A1* | 12/2016 | Malgat | ............... | A24F 40/70 |
| 2018/0249763 A1* | 9/2018 | Schmidt | ............... | F04B 19/006 |
| 2019/0246696 A1* | 8/2019 | Schmidt | ............... | A24F 40/50 |
| 2020/0008473 A1* | 1/2020 | Schmidt | ............... | A61M 15/0021 |

FOREIGN PATENT DOCUMENTS

| | | |
|---|---|---|
| DE | 10 2016 125 180 A1 | 6/2018 |
| DE | 10 2017 111 119 A1 | 11/2018 |
| EP | 2 764 783 | 8/2014 |
| EP | 3061358 A1 | 8/2016 |
| EP | 3078281 A1 | 10/2016 |
| WO | WO 2015/117700 A1 | 8/2015 |
| WO | 2018/083007 A1 | 5/2018 |
| WO | WO-2018/083007 | 5/2018 |
| WO | 2018/115109 A1 | 6/2018 |
| WO | WO-2018/115109 | 6/2018 |

OTHER PUBLICATIONS

Examination Report from German Patent Office for Application No. 10 2017 111 435.1, dated Jan. 15, 2018, pp. 1-5.
Third-Party Submission Under 37 C.F.R. §1.290, Feb. 27, 2019, pp. 1-99.

* cited by examiner

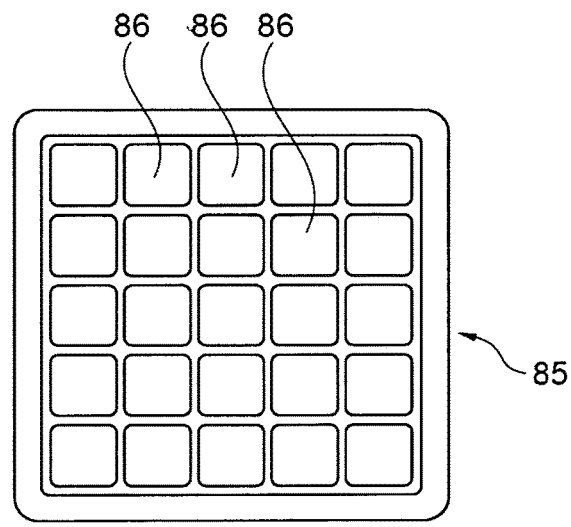
FIG. 5
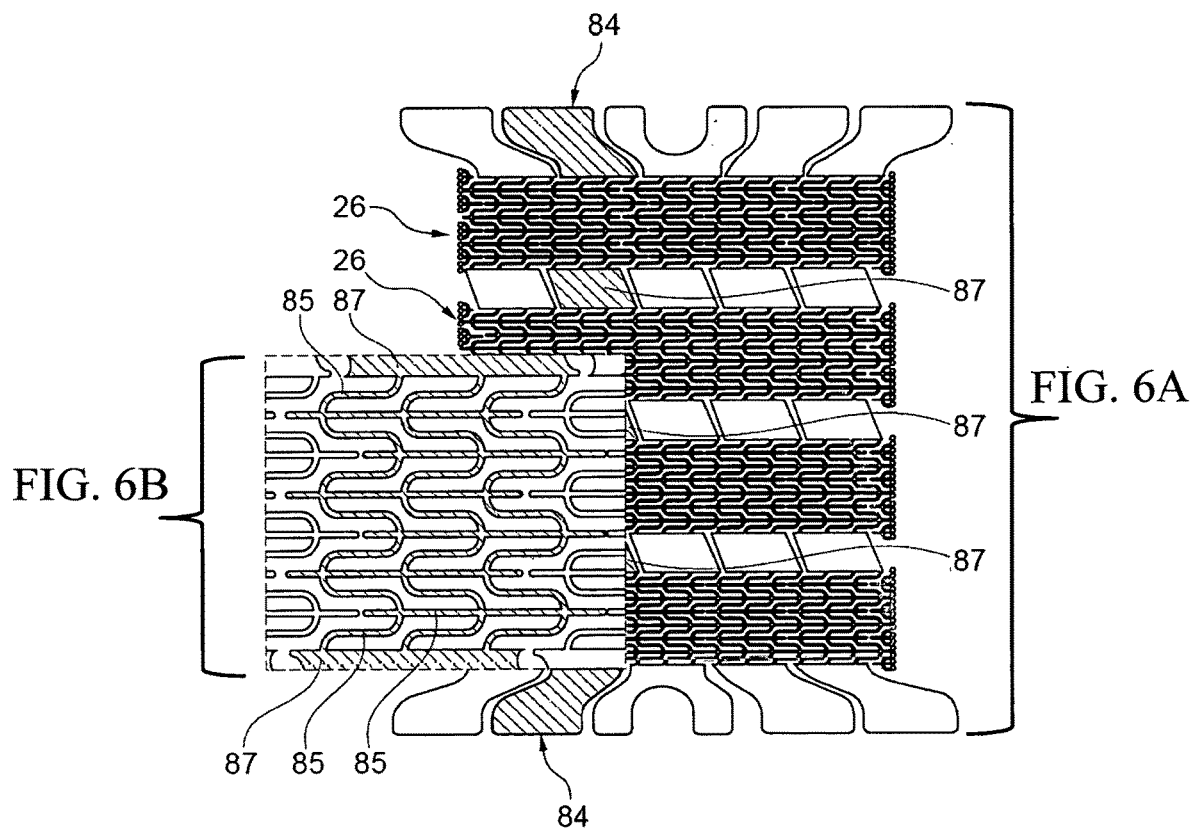
FIG. 6A
FIG. 6B

EVAPORATOR UNIT FOR AN INHALER AND METHOD FOR CONTROLLING AN EVAPORATOR UNIT

CROSS REFERENCE TO A RELATED APPLICATION

This application claims priority under 35 U.S.C. § 119(e) of German Patent Application No. DE 10 2017 111 435.1, filed May 24, 2017, which is incorporated herein by reference in its entirety.

FIELD OF THE INVENTION

The present invention relates to an evaporator unit for an inhaler comprising a heating element, the evaporator unit being designed to evaporate liquid, the evaporated liquid being taken up by an airflow flowing through the evaporator. The invention also relates to a method for controlling an evaporator unit.

BACKGROUND OF THE INVENTION

Conventional e-cigarettes consist of a wick, for example made of glass fibre or cotton, and a heating wire wound around the wick or a heating grid lying on the wick or surrounding the wick. The liquid is sucked into the wick and is evaporated therein by applying a voltage to the heating wire or the heating grid. This method has serious disadvantages. Firstly, the arrangement of the wick and heater varies depending on the manufacture. This means that a different amount of liquid and thus also nicotine is evaporated on each drag depending on the production model. Secondly, what are known as hot spots occur on the heater. Regions of the heater in which no liquid is available, weak points in the heating wire or structural defects in the heating grid, or particularly tightly wound regions of heating wires, become significantly hotter than the other regions of the heater. The specific resistance increases in said regions, which further increases the heating power, resulting overall in a significantly overheated point. This can lead to harmful decomposition products and what is known as "dry puff". Thirdly, the evaporation of the low-boiling liquid components results in the build-up of high-boiling components in the liquid in close proximity to the heater. In extreme cases, this can lead to the liquid boiling only away from this layer, and non-evaporated, high-boiling liquid being carried away from the layer close to the heater. This leads to inadvertent, explosion-like spraying of the liquid.

Current electronic cigarettes which build on the wick-coil principle, such as described in US 2016/0021930 A1, have various disadvantages. Firstly, there is no separation between liquid evaporation and dosing. Secondly, the amount of vapour and the heater temperature are directly linked, i.e. large amounts of vapour require high evaporation temperatures. Thirdly, there can be uneven temperature regions at/in the region of the evaporator, which runs the risk of local liquid overheating and of harmful substances being produced. Fourthly, the temperature in the evaporator region on the wick/coil surface differs from the core temperature in the wick, as a result of which there can be changes in the concentration of the liquid components during any given evaporation process or puff or drag. Furthermore, this change in concentration leads to a gradual change in the composition of the liquid remaining in the liquid store, i.e. the amount of active ingredient released is uneven and changes from drag to drag.

The primary function of e-cigarettes is that of producing an inhalable aerosol based on what are known as e-liquids. This involves the administered e-liquid being evaporated and the aerosol being produced by partial or complete re-condensation when mixing with the entrained airflow. The droplet size depends in this case on factors, inter alia condensation nuclei in the air and the cooling rate, which cannot be controlled or can be controlled only to a limited extent and which, during application, can lead to an increased intake of nicotine compared with conventional cigarettes, and thus to reduced satisfaction. The ability to influence the droplet sizes and compositions during the evaporation process would be desirable.

When evaporating e-liquids in conventional wick-coil evaporators of e-cigarettes, a glycerol-enriched composition is found in the wick, in which composition the gas phase composition corresponds to that of the subsequent liquid flow. Said composition also has a corresponding boiling point. A glycerol-enriched composition is found in the wick close to the heating coil, and is not constant along the wick. It can be seen in this case that higher boiling points have to occur in portions of the wick surrounding the heater than when the liquid has a constant composition in the vapour-formation region, i.e. when said liquid is well mixed. Furthermore, a composition gradient in the cross section of the wick can lead to spontaneous evaporation of liquid in the centre of the wick, which is difficult to control and leads to the release of large liquid droplets. This state should be avoided for an evaporation that is as even as possible at a temperature that is as low as possible in order to avoid thermal decomposition of the liquid.

Other evaporation methods in which the heat is introduced into the liquid by heated surfaces or solid walls also result in nucleate boiling or film boiling, and thus in locally significantly non-stationary evaporation processes which run the risk of the spontaneous release of large liquid droplets and local overheating, since the supply of heat and the formation of the gas phase are in conflict with one another.

US 2016/0007653 A discloses an evaporation structure in MEMS technology. In this case, the heater is positioned on a closed membrane such that the vapour outlet site and the heating site are separated. As such, the above-described explosion-like spraying of the liquid can also occur here. In addition, in this case a heater and a temperature sensor are mounted at separate points on said membrane, and therefore the local heater temperature cannot be directly measured. No details are provided in respect of the mode of operation, and therefore a continuous, non-pulsed operation has to be assumed. There is thus the risk of complete evaporation at the heater resulting in a subsequent significant increase in temperature. Economical manufacture and assembly, as well as coupling to temperature sensors and flow sensors, are cited as advantages of the application. Therefore, the above-described disadvantages of conventional e-cigarettes cannot be unequivocally remedied thereby.

The heating element of conventional e-cigarettes consists of a chromium-nickel wire, stainless steel or other metal alloys, for example. Said alloys are disadvantageous in that the specific resistance thereof increases with the temperature, and therefore poorly cooled regions exhibit increased resistance and thus require increased heating power. This self-reinforcing process leads to significantly inhomogeneous temperature distributions, which in turn cause an increased and uncontrolled release of harmful substances. In addition, the catalytic effect of the metals can lead to increased production of harmful substances.

BRIEF SUMMARY OF THE INVENTION

The object of the invention consists in providing an evaporation unit that works simply, reliably and reproducibly, by means of which liquid can be reliably and reproducibly transitioned into the gas phase.

The invention achieves this object by means of the features of the independent claims. According to the invention, the heating element is designed to heat the airflow and the evaporator is arranged downstream of the heating element, and the evaporator comprises at least one air-permeable capillary structure having a surface that can be wetted, at least in part, by liquid from the liquid store and is supplied with liquid by capillary action. On account of the automatic subsequent flow of liquid as a result of the capillary action of the capillary structure in order to compensate for evaporated liquid, a separate active feed mechanism can be omitted, which leads to reduced costs and reduces the required overall dimensions.

By means of the evaporator comprising the air-permeable capillary structure, which is arranged downstream of the heating element, it is possible to achieve extremely precise temporal control of the evaporation and dosing of the heating power and of the vapour.

In a preferred embodiment, the capillary structure consists of an electrically conductive material, at least in part. In this embodiment, the capillary structure can conduct electrical current, and thus transport energy and/or signals.

The capillary structure is preferably heatable. A heatable capillary structure allows the heating power required to evaporate the liquid to be split between the heating element and the capillary structure. Heating the capillary structure preferably causes general heating which approximately corresponds to the power required to heat the subsequent flow of liquid to a temperature close to, preferably below, a boiling point. Below a boiling point, the liquid is not evaporated and can be transported in the capillary structure and/or on the surface of the capillary structure by capillary action. The heating element can heat the air to a set temperature, preferably close to a boiling point of the liquid, particularly preferably above a boiling point, and can evaporate liquid located on the surface of the capillary structure. In other words, the liquid is preferably preheated in a controlled manner until just below the boiling point in the capillary structure. The heated air produced by the heating element then provides substantially only the difference in evaporation enthalpy required to achieve an input of heat into the liquid in order to exceed the evaporation threshold.

This embodiment is particularly preferred when the capillary structure is also electrically conductive. If the capillary structure is electrically conductive, the electrical resistance inherent in the capillary structure can be used to convert the electrical energy into thermal energy, and thus to heat the capillary structure in order to achieve the evaporation of the liquid on the surface of the capillary structure. Although the possible heat flux densities on the surface are smaller than in the case of nucleate boiling, this is compensated for by a correspondingly large surface area of the spatially structured capillary structure. This ensures that, in combination with the large surface area of the capillary structure and the integrated heater thereof, a desired amount of the liquid can be evaporated without resulting in overheating or nucleate boiling to an undesirable extent.

It is advantageous for the airflow to be heated to a temperature above a boiling point of the liquid mixture and/or to heat the capillary structure to a temperature below a boiling point of the liquid mixture and/or to a temperature of at least 100° C., preferably at least 150° C., more preferably at least 200° C. and even more preferably at least 250° C. Heating the temperature in the airflow to above a boiling point and/or heating the capillary structure to a temperature above a boiling point and/or above one of the specified values is used to achieve non-nucleate evaporation in the capillary structure and reliable feeding of liquid in/on the capillary structure.

It is advantageous for the capillary structure to be heatable by means of a first electrical/electronic unit, the first electrical/electronic unit being designed to control the heating element. This embodiment involves only one power electronics unit which jointly supplies the heating element and the capillary structure with electrical power. The power is preferably divided by adjusting the ratios of the electrical resistances of the heating element and the capillary structure. Temperature-dependent power consumption is possible by way of an appropriate selection of thermistors, i.e. heating materials having varying resistance-temperature behaviours. The resistances of the heating element and the capillary structure can be detected by measuring the particular drop in voltage. The power electronics unit is usually controlled by pulse-width modulation and supplied with power by a current source.

It is advantageous for a first electrical/electronic unit to be designed to control the heating element, and for the capillary structure to be heatable by means of a second electrical/electronic unit. The heating element is usually controlled by a power electronics unit by means of pulse-width modulation, which unit is in turn supplied with power by a current source. Ideally, the capillary structure is heated by intrinsic electrical heating, i.e. the ohmic resistance, in a manner controlled by a second power electronics unit. Providing two separate current sources for each of the first and the second electrical/electronic unit is also conceivable.

The capillary structure advantageously has a porosity of between 5-95%, preferably 10-90%, 15-85% or 20-80%, particularly preferably 30-70% or 35-65%, in the flow direction of the airflow and/or transversely to its preferably planar extension. Porosity in this case is understood to mean the ratio of free surface to material surface, for instance in terms of the proportion of the perforated area of the capillary structure for allowing the passage of the airflow.

The capillary structure is preferably non-woven or woven, in particular in the form of a folded or rolled woven metal fabric. This embodiment takes account of an inner surface that can be wetted by liquid and is ideally as large as possible owing to spatial structuring, by means of which surface a transfer of heat that is as effective and targeted as possible can be achieved between the capillary structure and the liquid. This embodiment is suitable for transporting liquid inside and/or on the surface of the capillary structure by capillary action.

The capillary structure is preferably a micromechanically produced structure (microelectromechanical structure or MEMS structure) comprising a substrate and channels and/or grooves running in the substrate. This embodiment results in a particularly large surface area of the capillary structure, which makes targeted evaporation possible. The targeted or untargeted insertion of channels and/or grooves makes the transport of liquid possible inside and/or on the surface of the capillary structure by capillary action.

The form and geometry of the structural elements of the capillary structure and/or of the heating structures of the heating element follow bionic structures, similar to microfibrils for example. Bionic structures have a particularly large surface area, which can be used in this case in a targeted manner for heating air and/or for providing liquid to be evaporated. Bionic structures can also be produced particularly efficiently and cost-effectively by suitable, self-organised processes.

The operating conditions of the capillary structure can preferably be measured using a sensor. This embodiment preferably allows for temperature monitoring by means of a temperature sensor, which can take place by detecting the electrical resistance of the capillary evaporator, if said evaporator has a suitable temperature coefficient, or by using an optional, dedicated temperature sensor. NTC and/or PTC thermistors can preferably be used for this purpose. Preferably, the pressure and/or flow speeds and/or concentrations characterising the operating state can also be measured, which state can be controlled as a result of the measurement.

The capillary structure and the liquid store are preferably connected by a connection means. This results in a spatial separation of the capillary structure and the liquid store, which can effectively present undesirable heating of the liquid in the liquid store.

The connection means is preferably designed to feed liquid by means of capillary action. The feeding of the liquid in the connection means by means of capillary action is advantageous in that the amount fed each time can be adjusted by configuring the underlying connection means, preferably such that, in operation, a precisely defined amount of liquid to be evaporated is fed, and such that direct and continuous coupling can be produced between the connection means and the capillary structure. In addition, a separate active feed mechanism can also be omitted here.

The connection means is preferably a nonwoven fabric. The fibres forming the nonwoven fabric can be arranged such that the connection means can take up a desired amount of liquid and/or supply said liquid to the capillary structure. The fibres forming the nonwoven fabric can be cotton, cotton wool or glass fibres. Other fibres and combinations can also be considered.

Particularly preferably, the connection means consists of an electrically insulating material. If the capillary structure is electrically heatable, this embodiment prevents the connection means also being actively heated. This in turn prevents the liquid located in the liquid store, to which the connection means is coupled, from heating up.

It is advantageous for the connection means to be encapsulated. Encapsulation of the connection means can prevent the liquid from evaporating inside and/or on the surface of the connection means. The liquid is not subjected to a secondary flow as a result of the encapsulation. This contributes to the reliable functioning of the capillary structure, in/on which the evaporation is intended to take place.

The liquid store is preferably arranged annularly around the evaporator. The annular, preferably circularly annular, arrangement of the liquid store and/or of the connection means allows the isotropic supply of the liquid into the capillary structure, thus allowing an even supply of the capillary structure with liquid from the liquid store, and particularly even evaporation of the liquid on the surface of the capillary structure.

Furthermore, a filter for filtering at least the air flowing through the primary air channel can preferably be provided downstream of the evaporator. The filter is advantageously arranged behind the evaporator tube so as to be spaced therefrom.

In one advantageous embodiment, the heating element and the evaporator are arranged in a primary air channel through which air flows, the primary air channel preferably being formed by the inner space of an evaporator tube that is open at both ends, preferably by an evaporator tube which allows free passage of a flow at the inlet and/or the outlet thereof. The evaporator unit preferably also comprises a secondary air channel in which air sucked into the evaporator unit flows whilst bypassing the heating element and the evaporator. Advantageously, at least portions of the secondary air channel extend in parallel with the primary air channel, preferably concentrically. The division of the airflow flowing into the evaporator unit into a primary airflow and a secondary airflow is advantageous in that not all of the airflow drawn in has to be heated to the temperature required for the droplet evaporation, meaning that heating power is saved and too high an outlet temperature is prevented. A re-mixing zone is preferably provided downstream of the evaporator, in which zone the heated primary airflow and the secondary airflow are mixed again. The evaporation and the subsequent re-condensation of the liquid can be influenced by the power of the air heating, the heating power of the capillary structure and the potential secondary air supply. This allows the droplet size to be set and influenced in a targeted manner.

The volumetric flow rate can preferably be set by means of the primary airflow and the secondary airflow. The ability to set the volumetric flow rates by means of the primary airflow channel and the secondary airflow channel can have a positive impact on the functioning of the evaporator unit, since flow speeds and heat transport depend on the volumetric flow rates. The setting ability, can preferably be realised actively and/or passively. An active setting ability means a setting ability that can be realised by control via an electronic/electrical unit. A passive setting ability means a setting ability that can be realised by one-off setting, for example by adjustment mechanisms or alternating components.

Embodiments without secondary air channels are conceivable, with all the air flowing through the evaporator unit then flowing through the primary air channel.

The primary air channel is particularly advantageously arranged inside the secondary air channel. This is favourable in terms of energy because the secondary air channel thermally insulates the primary air channel towards the outside. In particular, the primary air channel and the secondary air channel can be arranged concentrically to one another.

The secondary air channel is advantageously arranged adjacent to, preferably so as to be spaced from, the primary air channel. This embodiment allows for a wide range of geometric arrangements of the invention.

The flow cross section of the secondary air channel is preferably larger or smaller than the flow cross section of the primary air channel, in particular at the inlet and/or outlet of the secondary air channel. The airflow enriched with evaporated liquid downstream of the evaporator is advantageously guided in the evaporator unit having a steady or decreasing temperature. The secondary air channel preferably comprises an inlet and an outlet, the inlet preferably being arranged upstream of the heating element and/or upstream of the evaporator, and/or the outlet preferably being arranged downstream of the heating element and/or downstream of the evaporator.

Providing the secondary air channel also makes it possible to keep the external temperature of the evaporator unit and an inhaler provided with said unit low, and to concentrate the "hot evaporation zones" inside, as a result of which a possible risk of burning when holding the inhaler is minimised. The secondary air channel makes it possible to optimally select a desired drop spectrum, to utilise exhaust heat from the primary airflow and to realise an efficient mixing zone having optimum mixing conditions.

According to a further aspect of the invention, a method for controlling an evaporator unit as described above is provided.

Advantageously, the capillary structure and/or the heating element are heated in a non-continuous, in particular cyclic and/or pulsed manner. This can optimise the energy input into the heating element and optionally into the capillary structure, and allows needs-based heating when evaporation is intended to be achieved, along with control of the heating power, and can be useful for the subsequent feeding of the liquid. It is advantageous for the temporal heating voltage profile Uhk(t) or the temporal heating voltage profiles Uh(t) for the heating element and Uhk(t) for the capillary structure to be specified such that a subsequent flow of liquid is ensured on the basis of the temperature. The heating power can thus be set on the basis of the feed rate and/or the feed requirements. The amount of subsequently fed liquid preferably corresponds to the amount of evaporated liquid. Therefore, there is only a subsequent flow in the amount that has been evaporated. Setting the temperature is conceivable in all cases. More preferably, the heating power of the heating element and/or of the capillary structure is kept at an upper temperature limit. This allows for reliable evaporation with the proviso that there is no overheating, and/or no harmful thermal decomposition of the liquid to be evaporated and/or of the vapour occurs. Optimum evaporation of the liquid that is adapted to the components thereof can be ensured using any of the specified methods, and an undesirable production of decomposition products can be reliably avoided.

BRIEF DESCRIPTION OF THE DRAWINGS

The invention will be explained in the following on the basis of preferred embodiments and with reference to the attached drawings, in which:

FIG. 5 is a schematic cross-sectional view of a microfibril for a bionic structure; and FIGS. 6A-6B show a bionic heating structure made up of microfibrils according to FIG. 5 (FIG. 6A) and an enlarged detail of the heating structure (FIG. 6B).

DETAILED DESCRIPTION

Figure 1:
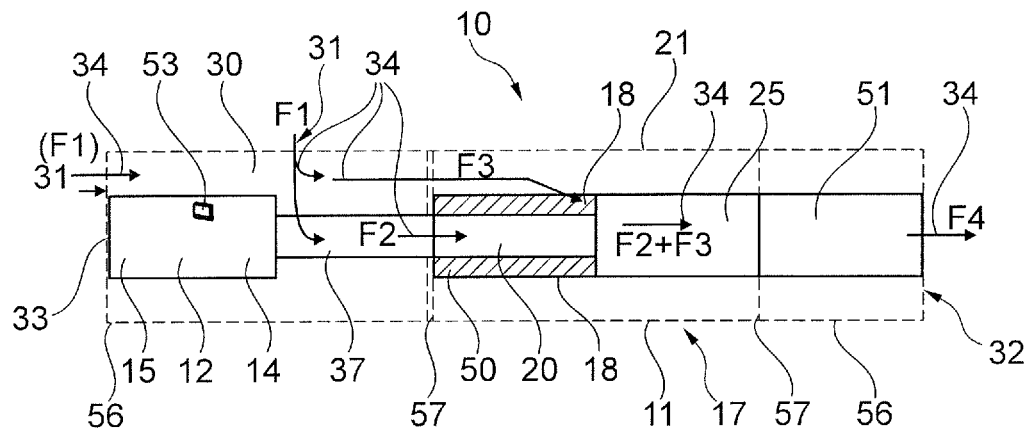
FIG. 1 is a schematic cross-sectional view of an electronic cigarette product in one embodiment of the invention.

The electronic cigarette product 10 includes a substantially rod-shaped or cylindrical housing 11. An air channel 30 is provided in the housing 11 between at least one air inlet opening 31 and the mouth end 32 of the cigarette product 10. The mouth end 32 of the cigarette product 10 refers to the end at which the consumer sucks for the purpose of inhalation, resulting in the cigarette product 10 being supplied with negative pressure and an airflow 34 being produced in the air channel 30. At least one air inlet opening 31 can be arranged on the shell side of the housing 11. In addition, or alternatively, at least one air inlet opening 31A can be arranged at the remote end 33 of the cigarette product 10. The remote end 33 refers to the end of the cigarette product 10 that is opposite the mouth end 32.

An air-heating means 37 for heating or preheating the incoming air is arranged downstream of one or the two air inlets 31, 31A in the flow path of the airflow 34. This can optimise the aerosol formation. The air-heating means 37 can for example be arranged adjacent to an energy supply unit 14, can extend in the circumferential direction around the inner side of the shell of the housing 11, can include a heater and/or is advantageously concentrically arranged.

The air sucked in through the inlet opening 31 is guided in the air channel 30, optionally via the interface or separating surface 57, to an evaporator unit 20. The evaporator unit 20 adds liquid 50 from the liquid store 18 into the airflow 34 in the form of small liquid droplets as a mist/aerosol and/or in gas-form as a vapour. An advantageous volume of the liquid store 18 is in the range of between 0.1 ml and 5 ml, preferably between 0.5 ml and 3 ml, more preferably between 0.7 ml and 2 ml or 1.5 ml. The liquid store 18 preferably has a closed surface and is preferably a flexible pouch in order to prevent the liquid from leaking, and thus includes a liquid tank. The supply of liquid is advantageously achieved by means of the evaporated amount of liquid, i.e. this is a design parameter of the capillary structure 40.

The geometric dimensions and the arrangement of the evaporator unit 20 in the inhaler 10 or the consumption unit 17 according to FIG. 1 is schematic and not to scale. In particular, the evaporator unit 20 may be substantially longer than shown in FIG. 1 and can extend for example over at least half the length of the inhaler 10.

The cigarette product 10 includes, preferably at the remote end of the cigarette product 10, the electronic energy supply unit 12 comprising an electrical energy store 14 and an electrical/electronic unit 15, i.e. for example a battery and a controller. The energy store 14 may in particular be an electrochemical disposable battery or a rechargeable electrochemical battery, e.g. a lithium-ion battery. The cigarette product 10 further includes a consumption unit 17 comprising a liquid store 18 and the evaporator unit 20. An electrical/electronic unit 19 (not shown) can also be arranged in the consumption unit 17.

In place of the separate electrical/electronic units 15, 19, a single electrical/electronic unit can be provided, which can be arranged either in the energy supply unit 12 or in the consumption unit 17. The electrical/electronic unit(s) of the cigarette product 10 is/are referred to the in the following as a whole as the control arrangement 29.

Advantageously, at least one sensor 7, for example a temperature sensor, is arranged in the housing 11, the function of which sensor will be explained below; see FIGS. 2 and 3. In addition, or alternatively, a pressure sensor or a pressure or flow switch may be provided, the control arrangement 29 being able to determine, on the basis of a sensor signal output by the sensor, an operating state of the cigarette product 10 in which a consumer sucks on the mouth end 32 of the cigarette product 10 in order to inhale. In said operating state, the control arrangement 29 actuates the evaporator unit 20 in order to add liquid 50 from the liquid store 18 into the airflow 34 in the form of small liquid droplets as a mist/aerosol and/or in gas-form as a vapour. The liquid is preferably added in a non-active manner.

The liquid (i.e. the liquid component mixture) stored in the liquid store 18 and intended for being dosed is for example a mixture of 1,2-propyleneglycol, glycerol and/or water, to which one or more flavours and/or active ingredients, such as nicotine, can be added.

The consumption unit 17 is advantageously designed as a cartridge 21 that can be replaced by the consumer, i.e. is designed as a disposable part. The remainder of the cigarette product 10, in particular containing the energy store 14, is advantageously designed as a base part 56 that can be reused by the consumer, i.e. is designed as a multi-use part. The cartridge 21 can be connected to the base part 56 and detached from the base part 56 by the consumer. A separating surface or interface 57 is thus formed between the cartridge 21 and the reusable base part 56. The cartridge housing 58 can form part of the housing 11 of the cigarette product 10.

In another embodiment (not shown), the consumption unit 17 is designed as a cartridge 21 that can be inserted into and removed from the base part 56 of the cigarette product 10 by the consumer. The cartridge housing is in this case a housing that is separate from the housing 11 of the cigarette product 10.

The cartridge 21 includes at least the liquid store 18. The cartridge 21 can include the electrical/electronic unit 19. In other embodiments, the electrical/electronic unit 19 is, in whole or in part, a fixed component of the base part 56. The evaporator unit 20 can also be part of the cartridge 21 or can be arranged in the base part 56. In some embodiments, therefore, the cartridge 21 can consist substantially of only the liquid store 18 and optionally the cartridge housing. Alternatively, the cartridge housing may be formed by the housing of the liquid store 18, and therefore a separate cartridge housing can be omitted.

In addition to the use in rod-shaped cigarettes products 10, the cartridge 21 can also be used in other inhalers, for example in electronic pipes, shishas, other heat-not-burn products, or in a medical inhaler. The energy store 14 is generally not part of the cartridge 21, but is part of the reusable base part 56.

The consumption unit 17 or the cartridge 21 advantageously includes a non-volatile information store 53 (see FIG. 1) for storing information or parameters relating to the consumption unit 17 (an ID chip) or the cartridge 21, for example in the form of an EEPROM or RFID, or in another suitable form. The information store 53 may be part of the electrical/electronic unit 19 or may be designed to be separate therefrom. Advantageously, the following information is advantageously stored in the information store 53: information relating to the ingredients, i.e. the composition of the liquid stored in the liquid store 18; information relating to the process profile, in particular to the power/temperature control; data relating to the state monitoring or system checking, for example leak testing; data relating to copy protection and forgery protection, in particular including an ID for unique labelling of the consumption unit 17 or the cartridge 21; serial number, date of manufacture and/or expiration date; and/or number of drags (number of inhalation drags by the consumer) or the usage time. Advantageously, the data store 53 is connected or connectable to the control means 15 of the base part 56 by means of contacts and/or lines.

Figure 2:
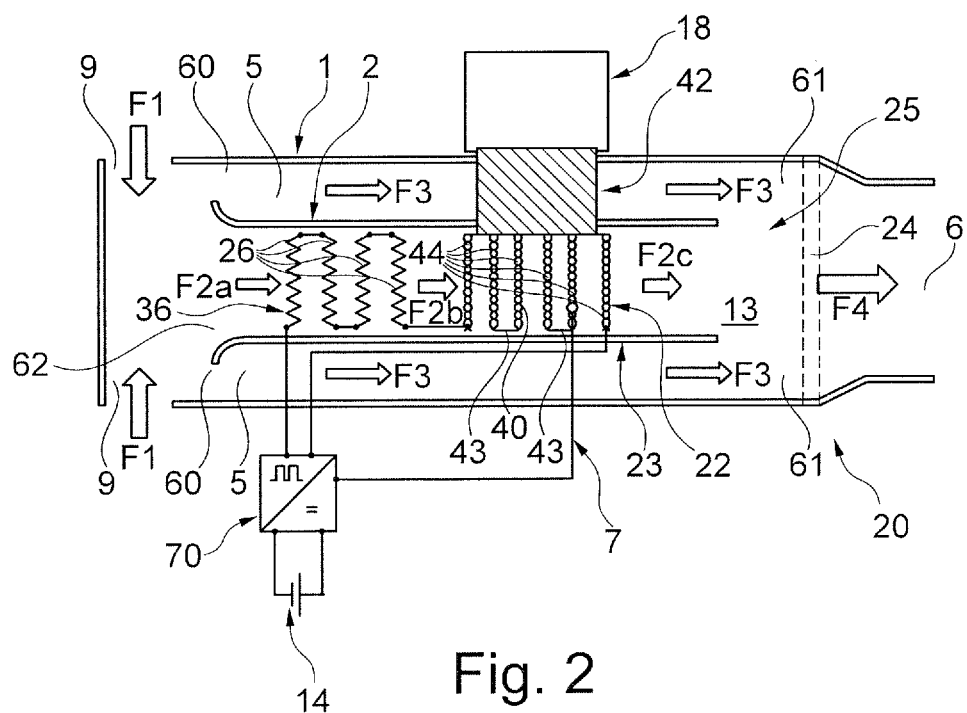
FIG. 2 is a schematic view of an evaporator unit according to the invention, together with a first electrical/electronic unit.
Figure 3:
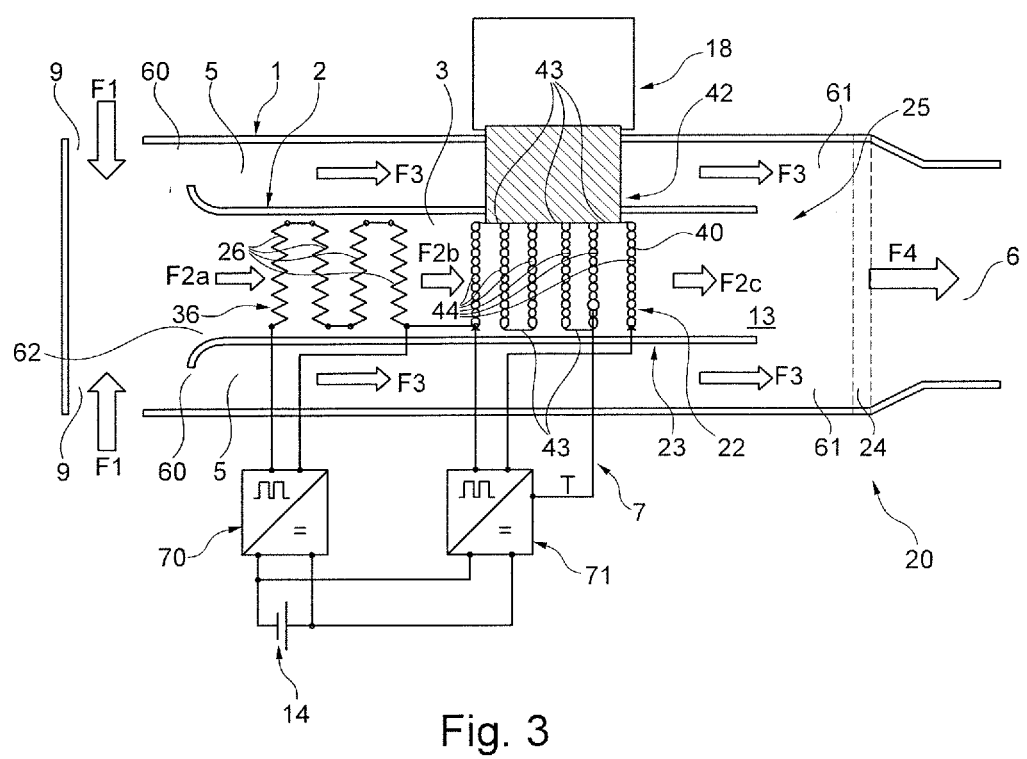
FIG. 3 is a schematic view of an evaporator unit according to the invention, together with a first and a second electrical/electronic unit.
Figure 4:
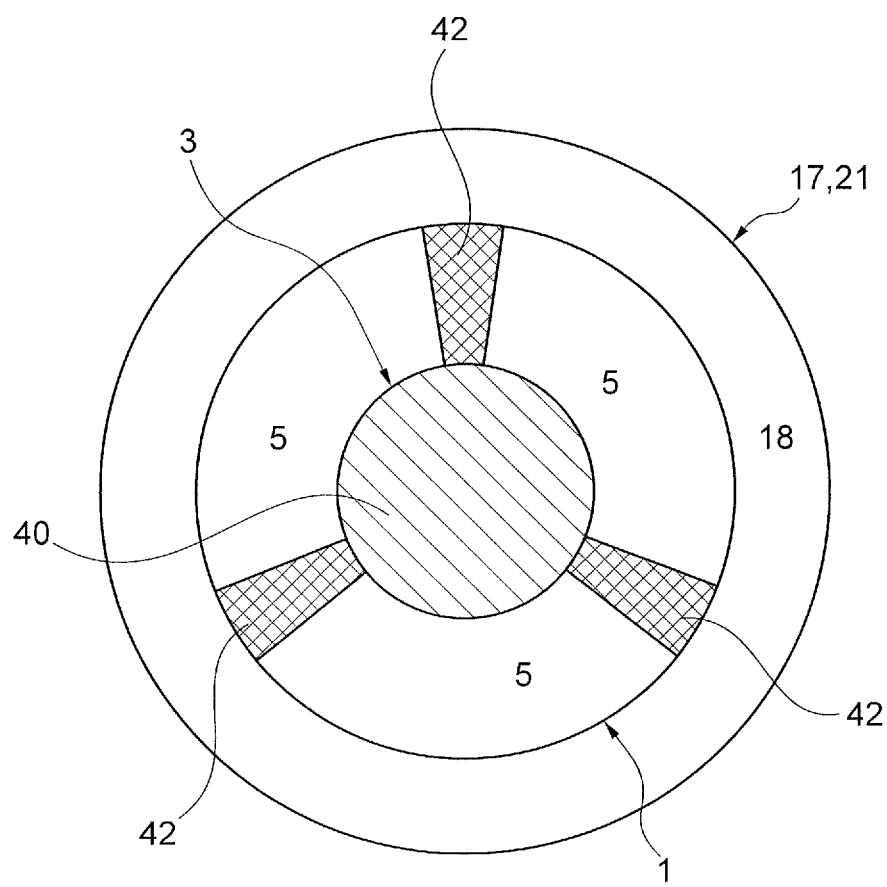
FIG. 4 is a schematic section through an evaporator unit together with a liquid store arranged concentrically therearound.

One advantageous embodiment of an evaporator unit 20 according to the invention is shown in FIG. 2.

The evaporator unit 20 can comprise its own housing 1; the housing 1 can alternatively be formed in whole or in part by the housing 11 of the cigarette product, however. The evaporator unit comprises at least one air inlet opening 9 for the inflow F1 of the air flowing through the evaporator unit 20 and at least one air output opening 6, the airflow 34, denoted by F1 to F4 in FIG. 2, flowing from the air inlet opening 9 to the air output opening 6 through the evaporator unit 20.

Inside the evaporator unit 20, the air channel 30 is split into two channels arranged in parallel with one another, namely into a primary air channel or heating channel 3, in which a heating element 36 is arranged, and a secondary air channel or bypass channel 5, in which a secondary airflow F3 can flow whilst bypassing the heating element 36. Accordingly, the optionally preheated airflow F1 flowing into the evaporator unit is split into a primary airflow F2a and a secondary airflow F3. In other words, part of the airflow F1 is guided around the evaporator 22 as the secondary airflow F3, and another part of the airflow F1, as the primary airflow F2, is guided through the evaporator 22 and is separated from the secondary flow by the evaporator tube 2.

The secondary air channel 5 comprises an inlet 60 and an outlet 61. The inlet 60 is arranged upstream of the heating element 36 and/or upstream of the evaporator 22. The outlet 61 is arranged downstream of the heating element 36 and/or downstream of the evaporator 22. Preferably, the primary air channel 3 is connected to a primary air inlet opening 62, which opening is arranged upstream of the heating element 36. The secondary air channel 5 is advantageously connected to the secondary air inlet opening 60, which opening is arranged upstream or downstream of the primary air inlet opening 62. The secondary air inlet opening 62 is arranged upstream or downstream of the evaporator 22.

The division of the airflow F1 flowing into the evaporator unit 20 into the primary airflow F2 and the secondary airflow F3 is advantageous in that the not all of the drawn-in airflow F1 has to be heated to the temperature required for droplet evaporation, thus saving heating power and preventing too high an outlet temperature.

The primary air channel 3 is advantageously arranged radially on the inside in the evaporator unit 20, and the secondary air channel 5 is arranged radially on the outside in said unit, i.e. is concentrically arranged, such that the secondary air channel 5 advantageously surrounds the primary air channel 3 around the circumference thereof. This is favourable in terms of energy, because the secondary air channel 5 thermally insulates the primary air channel 3 towards the outside. The primary channel 5 is advantageously formed by the inner space of an evaporator tube 2. The secondary air channel 5 is advantageously an annular channel, which is in particular formed between the flow tube 2 and the housing 1. The secondary air channel 5 and the primary air channel 3 are preferably arranged concentrically to one another. The housing 1 can take over the outer flow guidance for the secondary flow channel 5.

An evaporator 22 for adding liquid coming from the liquid store 18 and admixing said liquid with the primary airflow F2b heated by the heating element 36 is arranged downstream of the heating element 36 in the primary channel 3. For this purpose, the above-described evaporator 22 comprises a capillary structure 40. The capillary structure 40 preferably includes at least one structural element 44, preferably a plurality of structural elements 44, which are advantageously electrically interconnected by conducting elements 43. A plurality of structural elements 44 is preferably arranged one behind the other in the flow direction of the airflow F2b. A plurality of, for example, six arranged structural elements 44 are provided in the embodiments in FIGS. 2 and 3. The structural elements 44 are advantageously interconnected in series by conducting elements 43. the structural elements 44 may be in the form of a grid, a meander, a helix, a spiral, a mesh, or may be non-woven or woven, in particular in the form of a folded or rolled metal woven fabric or a micromechanically produced structure consisting of channels and grooves, and/or its form and structure is modelled on a bionic structure, such as microfibrils 85. In order to prevent harmful substances arising on account of catalytic effects and/or metal being released into the vapour/aerosol in the region of the capillary structure 40, the capillary structure 40 can also be designed to be metal-free, optionally as silicon, or polymeric silicon, or said structure can also be ceramic, metallic or semi-metallic, or can consist of graphite.

The capillary structure 40 produces a capillary action, i.e. evaporated liquid is automatically subsequently fed in the capillary structure 40. The capillary structure is in this case not limited to elongate capillaries, but can comprise pores or other cavities providing a capillary effect. In particular, bionic structures such as microfibrils 85 can also advantageously be used. The at least one structural element 44 and thus the capillary structure 40 of the evaporator 22 advantageously has a porosity, preferably a high porosity, which is determined by the mesh size and/or the size of the pores, channels or other cavities in the capillary structure. A high porosity requires a large surface area 41 which can be wetted by liquid and can then be evaporated. The porosity also ensures the required air-permeability of the structural elements 44 and thus that of the capillary structure 40, as well as the intended capillary action for feeding the liquid. A plurality of structural elements 44 can be arranged in parallel with or at an angle to one another. The at least one structural element 44 of the capillary structure 40 can have a spatially periodic, aperiodic, isotropic and/or anisotropic structure.

Upon detection of an airflow 34 through the air channel 30 caused by the consumer sucking, the control means 29 actuates the heating element 36 and the heatable capillary structure 40 in order to put the evaporation unit into operation. This is described in more detail below.

The primary airflow F2a initially flows through the electrical heating element 36, which heats the air up to a suitable temperature. The heating element 36 is controlled, for example by pulse-width modulation, by a first electrical/electronic unit 70, which preferably includes a power electronics unit. An electrical voltage Uh generated by the heating voltage source 14 is applied to the heating element 36 and leads to a flow of current through the heating element 36. This leads to the heating element 36 heating up as a result of the ohmic resistance of said element, and this leads to the air F2a flowing past the heating element 36 heating up. The heating element 36 preferably includes at least one heating structure 26, in this case a plurality of four heating structures 26 interconnected in series, for example. A grid structure is also conceivable.

In a preferred embodiment, the capillary structure 40 is also heatable. In the embodiment shown in FIG. 2, the capillary structure 40 is also controlled, for example by pulse-width modulation, by the first electrical/electronic unit 70, which preferably includes a power electronics unit. An electrical voltage UhK generated by the heating voltage source 14 is applied and leads to a flow of current through the heating element 36 and the capillary structure 40. This leads to the heating element 36 and the capillary structure 40 heating up as a result of the ohmic resistance of the heating element 36 and the capillary structure 40, and this leads to the air F2a flowing past the heating element 36 heating up, which air impinges on the heated capillary structure 40 in order to flow therearound and/or therethrough and to contribute to the evaporation.

Appropriate setting of the ohmic resistances of the structural elements 44 and the conducting elements 43 can be used to heat different structural elements 44 to the same or different temperatures. For example, the structural elements 44 can be heated to a greater extend downstream in order to counteract cooling in the evaporator caused by evaporation heat and diffusion. This results in particularly even evaporation, and undesirable condensation of already evaporated liquid can be prevented. Preferably, the sensor 7 positioned in or on the capillary structure 40 for measuring operating conditions, such as the temperature, of the capillary structure 40 is in contact with the first electrical/electronic control unit 70 and/or with other control elements which control the heating of the capillary structure 40. For example, the heating power of the capillary structure 40 and/or of the heating element 36 can be switched on or off at a given temperature. Other forms of control on the basis of the data detected by the sensor 7 is also possible, in particular temperature control. A plurality of sensors 7 can also be provided in the respective structural elements 44 or at other points on the evaporator 22 in order to determine temperature, pressure or concentration gradients, for example, and to implement corresponding control measures. Sensors can also be provided in/on the heating element 36 or can be formed thereby.

The temporal heating voltage profile Uhk(t) for the capillary structure can advantageously be specified such that a subsequent flow of liquid is ensured.

The temperature of the heated airflow F2b can be just above or below, by up to 40° C., the boiling point of the liquid that said liquid has following evaporation of a specified amount. This ensures that there can be rapid evaporation of the droplets up to this state, and the evaporation is not too slow. Advantageously, the air F2b should not be heated to a temperature above that allowing thermal decomposition of the components to be avoided.

The heated airflow may optionally be homogenised in terms of the flow and temperature profile thereof by a flow-homogenisation element (not shown) for example in the form of a grid or swirl elements. The flow-homogenisation element is preferably arranged in the primary air channel 3, more preferably between the heating element 36 and the evaporator 22.

The heated airflow F2b impinges on the liquid preheated in the capillary structure 40 and evaporates a particular amount of the liquid, which can be set using air temperature, volumetric flow rate and the (feeding) characteristics of the capillary structure 40. The evaporated liquid continues to flow along the airflow F2c as vapour or an aerosol. The capillary structure 40 may be arranged and oriented longitudinally with respect to the airflow F2*b* or transversely thereto, as long as targeted evaporation is ensured upstream of or in the airflow F2*c*.

Following addition from the evaporator 22, the advantageously preheated liquid, i.e. the liquid film, located on the surface 41 of the capillary structure 40 is evaporated substantially instantaneously as a result of the contact with the hot airflow F2*b*. In this way, an evaporator 22 is formed in the evaporator unit 20 or in the evaporator tube 2 or primary channel 3. The formation of the air/aerosol flow F2*c* also takes place in the zone 13 located downstream of the evaporator 22.

The vapour-containing primary airflow F2*c* is mixed with the secondary airflow F3 in the re-mixing zone or mixing region 25. Advantageously, the enriched core flow is kept away from the cool walls in the outlet, which prevents wall condensation. The combined, vapour-containing airflow F4 finally leaves the evaporator unit 20 preferably through a cooling region 51 and the outlet opening 6.

The connection means 42 connecting the evaporator 22 to the liquid store 18 can be formed by an electrically non-conductive nonwoven fabric. In this embodiment, the nonwoven fabric can be coupled to the capillary structure 40 in a mechanical or liquid-conducting manner and can thus allow transport of the liquid, induced by capillary action, out of the liquid store 18 into the capillary structure 40 via the connection means 42. In particular, the nonwoven fabric can have the same material properties and manufacturing steps as the structural elements 44 of the capillary structure 40. Other connection means 42 are also conceivable, however, and can be supplied with the required liquid volumetric flow from the liquid store 18 by means of a separate flow control means, e.g. a micropump or a valve. When using a valve structure having one or more valves, the liquid store 18 can advantageously be pressurised.

The liquid store 18, the connection means 42, the first electrical/electronic unit 70 and the optional second electrical/electronic unit 70 and the current supply 14 may be implemented in various spatial configurations. Furthermore, additional, controlled, electrical preheating of the liquid to be evaporated may also be implemented, as a result of which the vast majority of the heat required for the evaporation can be introduced and/or the liquid properties (surface tension/viscosity) can be influenced, which is relevant for the droplet-formation process and the feeding process. Said preheating may be incorporated in the evaporator 22 or in the connection means 42.

The temperature of the primary airflow F2b can be controlled by means of the measurement variable of the electrical resistance of the heating element, provided said resistance is temperature-dependent, or can be controlled directly using an optional sensor 7 in the homogenised primary airflow F2*b*.

A voltage curve Uh(t) that is adapted to the liquid mixture used is preferably stored in the data store 53 of the cartridge 21 or in a data store 59 of the base part 56. This makes it possible to specify the voltage profile UH(t) in a manner adapted to the liquid used, such that the heating temperature of the heating element 36 can be controlled, temporally throughout the evaporation process, according to the exactly known evaporation kinetics of the particular liquid, as a result of which optimum evaporation results can be obtained. The evaporation temperature is preferably in the range of between 100° C. and 400° C., more preferably between 150° C. and 350° C., yet more preferably between 190° C. and 240° C.

The evaporator unit 20 is set such that an advantageous amount of liquid is dosed in the range of between 1 μl and 20 μl, more preferably between 2 μl and 10 μl, yet more preferably between 3 μl and 5 μl, usually 4 μl per drag by the consumer. Preferably, the evaporation unit 20 can be set with respect to the amount of liquid per drag.

The evaporator 22 can advantageously be set such that primarily liquid droplets having a diameter in the range of between 0.05 μm and 5 μm, preferably between 0.1 μm and 3 μm, occur in the aerosol. Droplet sizes in the range of between 0.05 and 5 MMAD (mass median aerodynamic diameter), preferably between 0.1 and 3 MMAD, more preferably between 0.3 and 2 MMAD, yet more preferably between 0.4 and 1.5 MMAD, for example approximately 0.5 MMAD or 1 MMAD can be optimum. MMAD corresponds to an EU standard and is specified in μm.

The heating element 36 and/or the evaporator 22 are advantageously electrically actuated at a suitable actuation frequency, typically in the Hz or kHz range and for example between 1 Hz and 50 kHz, preferably between 30 Hz and 30 kHz, particularly preferably between 100 Hz and 25 kHz. In an alternative embodiment, the actuation frequency can be in the range of between 5 Hz and 50 Hz, preferably between 10 Hz and 40 Hz.

In a further embodiment, the heating element 36 and/or the evaporator 22 can be continuously actuated and/or controlled, in particular over portions of a drag or puff and/or a series of successive drags or puffs.

An alternative embodiment of the invention can be seen in FIG. 3. This embodiment has the characteristics of the embodiment shown in FIG. 2, but differs by the presence of a separate, second electrical/electronic unit 71 for controlling the heating of the capillary structure 40. This embodiment allows more targeted control of the heating element 36 and the capillary structure 40. Analogously to the first electrical/electronic unit 70, said second unit is advantageously controlled, for example by pulse-width modulation, in a time-variable manner. An electrical voltage Uhk generated by the heating voltage source 14 is applied and leads to a flow of current through the capillary structure 40. This leads to the capillary structure 40 heating up as a result of the ohmic resistance of said capillary structure. A second energy supply unit is conceivable. Further processes and components are analogous to the embodiment shown in FIG. 2.

FIG. 4 shows a section through a preferred embodiment of the invention. The consumption unit 17 includes a liquid store 18. The liquid store 18 is advantageously arranged annularly around the housing 1, in which the secondary air channel 5 is preferably located. The secondary air channel 5 preferably annularly surrounds the primary air channel 3, in which the capillary structure 40 is located. The connection means 42 advantageously includes a plurality of elements (three elements in FIG. 4) connecting the liquid store 18 to the capillary structure 40. The uniform arrangement of the elements of the connection means 42 allows an isotropic supply of liquid to the capillary structure. In this embodiment, the elements of the connection means 42 extend through the secondary air channel 5 and are preferably encapsulated.

Alternative embodiments of the heating structure 26 are shown in FIG. 5 and FIGS. 6A-6B. The form of said structure having heat conductors 85 follows bionic structures, as can be found in the form of microfibrils in particular in wood fibre cells or trachea; see FIG. 5. The capillary structure 40 having the structural elements 44 and/or the connection means 42 can also advantageously follow, in terms of form, the form of microfibrils. Advantageous dimensions of the channels 86 between the heat conductors 85, i.e. the free space between adjacent heating structures 85, are in the range of between 10 μm and 0.5 mm, more advantageously between 15 μm and 150 μm.

A bionic heating structure 26 having correspondingly formed and spaced heat conductors 85, which can be interconnected in series by conducting portions 87, is shown in FIG. 6A. FIG. 6B shows an enlarged detail of FIG. 6A in the region of a heating structure 26. As can be seen in FIGS. 6A and 6B, the advantageous, net-like linkage of the heat conductors 85 or the heating element geometry results in a dense surface structure having a large area coverage, which allows particularly rapid and efficient evaporation of liquid. Electrodes 84 can be connected to the heating element 36 in order to apply the heating voltage Uh thereto.

EMBODIMENTS

1. Evaporator unit (20) for an inhaler comprising a heating element (36), the evaporator unit (20) being designed to evaporate liquid, the evaporated liquid being taken up by an airflow flowing through the evaporator unit (20), characterised in that the evaporator unit (20) comprises at least one air-permeable capillary structure (40) having a surface (41) that is heatable in order to preheat the liquid and can be wetted, at least in part, by liquid and is supplied with liquid by capillary action, the heating element (36) being designed to heat the airflow flowing through the evaporator unit (20), the capillary structure (40) being arranged downstream of the heating element (36) such that the heated airflow leads to evaporation of the preheated liquid.

2. Evaporator unit (20) according to Embodiment 1, characterised in that the capillary structure (40) consists of an electrically conductive material.

3. Evaporator unit according to Embodiment 2, characterised in that heating element (36) is designed to heat the airflow to a temperature above a boiling point of the liquid mixture, and/or in that the capillary structure (40) is designed to heat the liquid to a temperature below a boiling point of the liquid mixture and/or to a temperature of at least 100° C., preferably at least 150° C., more preferably at least 200° C. and even more preferably at least 250° C.

4. Evaporator unit according to any of the preceding Embodiments, characterised in that the capillary structure (40) is heatable by means of a first electrical/electronic unit (70), the first electrical/electronic unit (70) being designed to control the heating element (36).

5. Evaporator unit according to any of the preceding Embodiments, characterised in that a first electrical/electronic unit (70) is designed to control the heating element (36), and the capillary structure (40) is heatable by means of a second electrical/electronic unit (71).

6. Evaporator unit according to any of the preceding Embodiments, characterised in that the capillary structure (40) is non-woven or woven, in particular in the form of a folded or rolled woven metal fabric.

7. Evaporator unit according to any of the preceding Embodiments, characterised in that the capillary structure (40) is a micromechanically produced structure comprising a substrate and channels and/or grooves running in the substrate.

8. Evaporator unit according to any of the preceding Embodiments, characterised in that the form and geometry of the structural elements (44) of the capillary structure (40) and/or of the heating structures (26) of the heating element (36) follows bionic structures, similar to microfibrils (85) for example.

9. Evaporator unit according to any of the preceding Embodiments, characterised in that at least one operating condition, for example the temperature, of the capillary structure (40) can be measured using a sensor (7).

10. Evaporator unit according to any of the preceding Embodiments, characterised in that the capillary structure (40) can be connected to a liquid store (18) by a connection means (42).

11. Evaporator unit according to Embodiment 10, characterised in that the connection means (42) is designed to feed liquid by means of capillary action.

12. Evaporator unit according to either Embodiment 10 or Embodiment 11, characterised in that the connection means (42) is a non-woven fabric.

13. Evaporator unit according to any of Embodiments 10 to 12, characterised in that the connection means (42) consists of an electrically insulating material.

14. Evaporator unit according to any of Embodiments 10 to 13, characterised in that the connection means (42) is encapsulated.

15. Evaporator unit according to any of the preceding Embodiments including a liquid store (18), characterised in that the liquid store (18) is arranged annularly around the evaporator (22).

16. Evaporator unit according to any of the preceding Embodiments, characterised in that a mixing zone (25) is provided downstream of the evaporator (22), in which zone a primary airflow F2 in particular enriched with evaporated liquid is mixed with a secondary airflow F3.

17. Evaporator unit according to Embodiment 16, characterised in that the volumetric flow rate can be set by means of the primary airflow F2 and the secondary airflow F3.

18. Evaporator unit (20) according to any of the preceding Embodiments, characterised in that the heating element (36) and the evaporator (22) are arranged in an air-permeable primary air channel (3).

19. Evaporator unit according to Embodiment 18, characterised in that the primary air channel (3) is formed by the inner space of an evaporator tube (2) that is open at both ends, preferably an evaporator tube which allows free passage of a flow at the inlet and/or the outlet thereof.

20. Evaporator unit according to any of the preceding Embodiments, characterised in that the evaporator unit (20) comprises a secondary air channel (5) in which air sucked into the evaporator unit (20) flows whilst bypassing the heating element (36) and the evaporator (22).

21. Evaporator unit according to Embodiment 20, characterised in that the secondary air channel (5) comprises an inlet (60) and an outlet (61), the inlet (60) preferably being arranged upstream of the heating element (36) and/or upstream of the evaporator (22) and/or the outlet (61) being arranged downstream of the heating element (36) and/or downstream of the evaporator (22).

22. Evaporator unit according to Embodiments 18 and 20, characterised in that the primary air channel (3) is arranged inside the secondary air channel (5).

23. Cartridge (21) comprising a liquid store (18) and an evaporator unit (20) according to any of the preceding Embodiments.

24. Inhaler (10) comprising an evaporator unit (20) according to any of the preceding Embodiments.

25. Method for controlling an evaporator unit (20) according to any of Embodiments 1 to 26. Method according to Embodiments 25, characterised in that the capillary structure (40) and/or the heating element (36) are heated in a non-continuous, in particular pulsed manner.

27. Method according to either claim 25 or claim 26, characterised in that a temporal heating voltage profile Uhk(t) for the capillary structure (40) is specified such that a subsequent flow of liquid is ensured.

28. Method according to any of Embodiments 25 to 27, characterised in that the heating power of the heating element (36) and/or of the capillary structure (40) is kept at an upper temperature limit.

29. Method according to any of Embodiments 25 to 28, characterised in that the heating power of the heating element (36) and/or of the capillary structure (40) is controlled such that evaporation is ensured according to temperature specifications.

The invention claimed is:
1. An evaporator unit for an inhaler, comprising:
a heating element,
wherein the heating element is configured to heat an airflow flowing through the evaporator unit; and
an evaporator;

wherein the evaporator comprises a capillary structure having a capillary structure surface that is configured to be wetted, at least in part, by a liquid supplied via capillary action, wherein the capillary structure is air-permeable, wherein the capillary structure is electrically conductive and the electrical resistance inherent in the capillary structure is used to convert electrical energy into thermal energy via a flow of current through the capillary structure so that the capillary structure surface is heated such that the liquid is preheated to produce a preheated liquid, wherein the capillary structure is arranged in the airflow downstream of the heating element, such that the airflow, after being heated by the heating element evaporates the preheated liquid to produce evaporated liquid, wherein the evaporated liquid is taken up by the airflow flowing through the evaporator unit, and wherein:
  (i) the capillary structure is heated by a first electrical/electronic unit via the first electrical/electronic unit providing the flow of current through the capillary structure, and the first electrical/electronic unit is configured to control the heating element; or
  (ii) a first electrical/electronic unit is configured to control the heating element, and the capillary structure is heated by a second electrical/electronic unit via the second electrical/electronic unit providing the flow of current through the capillary structure.

2. The evaporator unit according to claim 1,
wherein the liquid is a liquid component mixture,
wherein:
  (i) the heating element is configured to heat the airflow flowing through the evaporator unit to a temperature above a boiling point of the liquid component mixture;
  (ii) the capillary structure is configured to heat the liquid to a temperature below a boiling point of the liquid component mixture; or
  (iii) the heating element is configured to heat the airflow flowing through the evaporator unit to a temperature above a boiling point of the liquid component mixture, and the capillary structure is configured to heat the liquid to a temperature below a boiling point of the liquid component mixture,
wherein the evaporated liquid is in the form of:
  (a) small liquid droplets as a mist/aerosol;
  (b) a vapor; or
  (c) small liquid droplets as a mist/aerosol, and a vapor.

3. The evaporator unit according to claim 1,
wherein the capillary structure comprises at least one capillary structure structural element,
wherein each capillary structure structural element of the at least one capillary structure structural element:
  (a) is woven; or
  (b) is a micromechanically produced structure comprising a substrate and channels and/or grooves running in the substrate.

4. The evaporator unit according to claim 1, further comprising:
a connector,
wherein the capillary structure is configured to be connected to a liquid store by the connector.

5. The evaporator unit according to claim 4,
wherein the connector is configured to feed the liquid from the liquid store to the capillary structure via capillary action.

6. The evaporator unit according to claim 4,
wherein:
  (i) the connector is a non-woven fabric;
  (ii) the connector consists of an electrically insulating material; or
  (iii) the connector is encapsulated.

7. The evaporator unit according to claim 1, further comprising:
the liquid store,
wherein the liquid store is arranged annularly around the evaporator.

8. The evaporator unit according to claim 1,
wherein a mixing zone is provided downstream of the evaporator,
wherein a primary airflow F2 is mixed with a secondary airflow F3 in the mixing zone, and
wherein the primary airflow F2 is enriched with the evaporated liquid.

9. The evaporator unit according to claim 8,
wherein a volumetric flow rate is settable via the primary airflow F2 and the secondary airflow F3.

10. The evaporator unit according to claim 1,
wherein the heating element and the evaporator are arranged in an air-permeable primary air channel.

11. The evaporator unit according to claim 10,
wherein the air-permeable primary air channel is formed by an inner space of an evaporator tube that is open at both ends and allows free passage of a flow at an inlet and/or an outlet thereof.

12. The evaporator unit according to claim 10,
wherein the primary air channel is arranged inside the secondary air channel.

13. The evaporator unit according to claim 1, further comprising:
a secondary air channel in which air sucked into the evaporator unit flows whilst bypassing the heating element and the evaporator.

14. The evaporator unit according to claim 13,
wherein the secondary air channel comprises a secondary air channel inlet and a secondary air channel outlet, and
wherein the inlet is arranged upstream of the heating element and/or upstream of the evaporator and/or the outlet being arranged downstream of the heating element and/or downstream of the evaporator.

15. The evaporator unit according to claim 1, further comprising:
a temperature sensor,
wherein the temperature sensor measures a temperature of the capillary structure.

16. A cartridge, comprising:
an evaporator unit according to claim 1; and
a liquid store.

17. An inhaler, comprising:
an evaporator unit according to claim 1.

18. A method for controlling an evaporator unit, comprising:
providing an evaporator unit according to claim 1; and
controlling:
  (A) a heating element heating power of the heating element, such that:
    (i) the heating element is heated in a non-continuous manner;

(ii) the heating element is kept at a heating element upper temperature limit; or (iii) evaporation of the liquid is ensured according to temperature specifications;

(B) a capillary structure heating power of the capillary structure, such that:

(i) the capillary structure is heated in a non-continuous manner;

(ii) the capillary structure is kept at a capillary structure upper temperature limit; or (iii) evaporation of the liquid is ensured according to temperature specifications; or (C) a heating element heating power of the heating element and a capillary structure heating power of the capillary structure, such that:

(i) the heating element is heated in a non-continuous manner, and the capillary structure is heated in a non-continuous manner;

(ii) the heating element is kept at a heating element upper temperature limit, and the capillary structure is kept at a capillary structure upper temperature limit; or (iii) evaporation of the liquid is ensured according to temperature specifications.

19. The evaporator unit according to claim 1, wherein the capillary structure is heated by a first electrical/electronic unit via the first electrical/electronic unit providing the flow of current through the capillary structure, and the first electrical/electronic unit is configured to control the heating element.

20. The evaporator unit according to claim 1, wherein a first electrical/electronic unit is configured to control the heating element, and the capillary structure is heated by a second electrical/electronic unit via the second electrical/electronic unit providing the flow of current through the capillary structure.

* * * * *